(12) United States Patent
Lafitte et al.

(10) Patent No.: US 9,804,123 B2
(45) Date of Patent: Oct. 31, 2017

(54) ELECTROCHEMICAL SENSOR UTILISING A DUAL REDOX SYSTEM CONTAINED WITHIN A SINGLE MOLECULE

(75) Inventors: Valerie Lafitte, Cambridge (FR); Nathan Lawrence, Huntingdon (GB)

(73) Assignee: SCHLUMBERGER TECHNOLOGY CORPORATION, Cambridge, MA (US)

( * ) Notice: Subject to any disclaimer, the term of this patent is extended or adjusted under 35 U.S.C. 154(b) by 129 days.

(21) Appl. No.: 13/001,964

(22) PCT Filed: May 1, 2009

(86) PCT No.: PCT/GB2009/001101
§ 371 (c)(1),
(2), (4) Date: Mar. 15, 2011

(87) PCT Pub. No.: WO2010/001082
PCT Pub. Date: Jan. 7, 2010

(65) Prior Publication Data
US 2011/0162977 A1 Jul. 7, 2011

(30) Foreign Application Priority Data
Jul. 3, 2008 (GB) .................................. 0812180.8

(51) Int. Cl.
*G01N 27/48* (2006.01)

(52) U.S. Cl.
CPC .................................. *G01N 27/48* (2013.01)

(58) Field of Classification Search
CPC ........... G01N 27/4167; G01N 27/3335; G01N 27/3277; G01N 27/48
USPC ...................................................... 205/787.5
See application file for complete search history.

(56) References Cited

U.S. PATENT DOCUMENTS

| 5,223,117 | A | * | 6/1993 | Wrighton et al. ............ 204/415 |
| 6,451,603 | B1 | | 9/2002 | Atkins et al. |
| 7,339,160 | B2 | | 3/2008 | Raghuraman et al. |
| 2003/0206026 | A1 | | 11/2003 | Diakonov et al. |
| 2006/0054501 | A1 | | 3/2006 | Jiang et al. |

(Continued)

FOREIGN PATENT DOCUMENTS

| GB | 2362469 A | 11/2001 |
| GB | 2404252 A | 1/2005 |

(Continued)

OTHER PUBLICATIONS

Redox-Sensitive Copolymer: A Single-Component pH Sensor Kay L. Robinson and and Nathan S. Lawrence Analytical Chemistry 2006 78 (7), 2450-2455.*

(Continued)

*Primary Examiner* — Louis Rufo (57) ABSTRACT

An electrochemical sensor utilizes a chemical compound which is not a macromolecule but rather is a single chemical compound of determinate structure, incorporating two redox systems which differ in their response to a species to be detected. In one form, one redox system displays a voltammetric wave which is pH dependent while another displays a voltammetric wave which is pH independent and acts as an internal reference. The sensor comprises a solid substrate, which may be carbonaceous, on which the compound is immobilized. The sensor may be incorporated into a tool to be suspended in a wellbore.

18 Claims, 8 Drawing Sheets

(56) References Cited

U.S. PATENT DOCUMENTS

| | | | |
|---|---|---|---|
| 2006/0211005 A1* | 9/2006 | Yaku et al. | ............... 435/6 |
| 2007/0065337 A1 | 3/2007 | Jiang et al. | |
| 2007/0272552 A1 | 11/2007 | Jiang et al. | |
| 2008/0023328 A1 | 1/2008 | Jiang et al. | |
| 2008/0035481 A1 | 2/2008 | McCormack et al. | |

FOREIGN PATENT DOCUMENTS

| | | |
|---|---|---|
| GB | 2409902 A | 7/2005 |
| GB | 2430749 A | 4/2007 |
| WO | WO2004005397 A1 | 1/2004 |
| WO | WO2005066618 A1 | 7/2005 |
| WO | WO2005085825 | 9/2005 |
| WO | WO2006113440 A2 | 10/2006 |
| WO | WO2007034131 A1 | 3/2007 |

OTHER PUBLICATIONS

"Redox-Sensitive Copolymer: A Single-Component pH Senso"r Kay L. Robinson and and Nathan S. Lawrence Analytical Chemistry 2006 78 (7), 2450-2455.*

Henry C Leventis, Ian Streeter, Gregory G Wildgoose, Nathan S Lawrence, Li Jiang, Timothy G.J Jones, Richard G Compton, Derivatised carbon powder electrodes: reagentless pH sensors, Talanta, vol. 63, Issue 4, Jul. 8, 2004, pp. 1039-1051, ISSN 0039-9140, 10.1016/j.talanta.2004.01.017.*

Butler et al: "Ferrocenyl-substituted fluorescent anthracenes and anthraquinones"; Tetrahedron Letters 45 (2004) 467-472.*

Masaki Murata ,Takako Fujita, Mami Yamada, Masato Kurihara, Hiroshi Nishihara. "Novel Protonation-Induced Structural Conversion of an Ethynylene-Bridged Ferrocene-Anthraquinone Complex" Chemistry Letters vol. 29 (2000) No. 11 p. 1328-1329.*

Smita Sarkar and and S. Sampath, "Stepwise Assembly of Acceptor—Sigma Spacer—Donor Monolayers: Preparation and Electrochemical Characterization" Langmuir 2006 22 (7), 3388-3395.*

Turner et al (eds) "Biosensors: fundamentals and applications". Oxford University Press, pp. 135-179 (1987).

Komaba et al: "Potentiometric biosensor for urea based on electropolymerized electroinactive polypyrrole"; Electrochim. Acta, 42 (1997) 383.

Stred'ansky et al: "Amperometric pH-sensing biosensors for urea, penicillin, and oxalacetate"; Anal Chim. Acta, 415 (2000) pp. 151-157.

Liu et al: "pH-Switchable, Ultrathin Permselective Membranes Prepared from Multilayer Polymer Composites"; J Am. Chem. Soc., 119 (1997) 8720.

"Cheng et al ""Permselectivity, Sensitivity, and Amperometric pH Sensing at Thioctic Acid Monolayer Microelectrodes""; Anal. Chem, 68 (1996) 4180".

Kirstein et al: "Enzyme Electrode for Urea with Amperometric Indication: Part 1—Basic Principle"; Biosensors, 1 (1985) 117.

Vostiar et al: "Amperometric urea biosensor based on urease and electropolymerized toluidine blue dye as a pH-sensitive redox probe"; Bioelectrochem., 56 (2002) 113.

Cui et al: Nanowire nanosensors for Highly Selective and Selective Detection of Biological and Chemical Species, Science, 293 (2001) 1289.

Baucke, F. G. K.: "The Glass Electrode—Applied Electrochemistry of Glass Surfaces"; J. Non-Cryst Solids, 73 (1985) 215.

Palleschi et al: "Bioelectrochemical Determination of Lactic and Malic acids in Wine"; Talanta, 41 (1994) 917.

Aquino-Binag et al: "Fabrication and Characterization of a Hydroquinone-Functionalized Polypyrrole Thin-Film pH Sensor"; Chem. Mater, 8 (1996) 2579.

Janata, J: "Potentiometric microsensors"; Chem. Rev., 90 (1990) 691.

Allongue et al: "Covalent Modification of Carbon Surfaces by Aryl Radicals Generated from the Electrochemical Reduction of Diazonium Salts"; J. Am. Chem. Soc. 1997, 119, 201-207.

"Andrieux et al: ""Derivatization of Carbon Surfaces by Anodic Oxidation of Arylacetates: Electrochemical Manipulation of the Grafted Films"""; J. Am. Chem. Soc. 1997, 119, 4292-4300".

Antoniadou et al: "Anion exchange activity of electrochemically bonded ethylene diamine on carbon fibres"; Journal of Applied Electrochemistry vol. 22 pp. 1060-1064 (1992).

Barbier et al: "Electrochemical bonding of amines to carbon fiber surfaces toward improved carbon-epoxy composites"; J. Electrochem. Soc., vol. 137, No. 6, Jun. 1990.

Bard et al "Electrochemical Methods: Fundamentals and Applications" (2nd ed. Wiley, 2001) pp. 226-252, 275,293-301 and 640-644.

Elshahawi et al: "Accurate measurement of the hydrogen sulfide content in formation fluid samples—case studies"; SPE paper 94707 (2005).

Guo et al : "Modification of a glassy carbon electrode with diols for the suppression of electrode fouling in biological fluids"; Chem. Pharm.Bull 44 860-862 (1996).

Hayes et al: "Preservation of NADH Voltammetry for Enzyme-Modified Electrodes Based on Dehydrogenase"; Anal. Chem. 1999, 71, 1720-1727.

Hickman et al: "Molecular Self-Assembly of Two-Terminal, Voltammetric Microsensors with Internal References"; Science, 25 (1991) p. 668.

Ioffe et al: "Selective reduction of aliphatic nitro-compounds with other functional groups"; Russ. Chem Rev., 35 (1966) 19.

Korostynska et al: "Review on State-of-the-art in Polymer Based pH Sensors"; Sensors 2007, 7, 3027-3042.

Lawrence et al: "Ferrocene sulfonates as electrocatalysts for sulfide detection"; Electrochimica Acta, 52 (2006) 499-503.

Lawrence et al: Comparison of the Electrochemical Reactivity of Electrodes Modified with Carbon Nanotubes from Different Sources; Electroanalysis 2005, 17, No. 1 pp. 65-72.

Lawrence et al: "Electrochemical determination of hydrogen sulfide at carbon nanotube modified electrodes"; Analytica Chimica Acta 517 (2004) 131-137.

Lawrence et al: "Triple Component Carbon Epoxy pH Probe"; Electroanalysis, 19 (2007) pp. 424-428.

Lawrence N S:"Amperometric Detection of Sulfide: An Electrocatalytic Reaction with Ferrocene Carboxylate"; Electroanalysis vol. 8, pp. 1658-1663 (2006).

Leventis et al: "Derivatised carbon powder electrodes: reagentless pH sensors"; Talanta 63 1039 (2004).

Pandurangappa et al: "Homogeneous chemical derivatisation of carbon particles: a novel method for funtionalising carbon surfaces"; Analyst, vol. 127, p. 1568 (2002).

Roberts R.M.G.: "Synthesis of ferrocenyl derivatives of anthracene"; Journal of Organometalic Chemistry, 388 (1990) 181-186.

Robinson et al: "A Vinylanthracene and Vnylferrocene-Containing Copolymer: A New Dual pH/Sulfide Sensor"; Electroanalysis 18, 2006, No. 7, 677-683.

Robinson et al: "Sulfide sensing via differential counter ion diffusion rates through redox-modulated poly (vinylferrocene) microparticles"; Electrochem Commun vol. 8 p. 1055-1061 (2006).

Sandhyarani et al: "Current understanding of the structure, phase transitions and dynamics of self-assembled monolayers on two- and threedimensional surfaces"; Int. Reviews in Physical Chemistry, 2003 vol. 22, No. 2, 221-262.

Robinson et al: "Redox-Sensitive Copolymer: A Single-Component pH Sensor"; Anal. Chem. 2006, 78, 2450-2455.

Santos et al: "Liquid Chromatography/Electrochemical Detection of Carbohydrates at a Cobalt Phthalocyanine Containing Chemically Modified Electrode"; Anal. Chem. 1987, 59, 1766-1770.

Streeter et al: "A sensitive reagentless pH probe with a ca. 120 mV/pH unit response"; J Solid State Electrochem., 8 (2004) 718.

Tustin et al: "Synthesis and characterisation of water soluble ferrocenes: Molecular tuning of redox potentials"; Journal of Organometallic Chemistry 692 (2007) 5173-5182.

Wildgoose et al: "Abrasively Immobilised Multiwalled Carbon Nanotube Agglomerates: A Novel Electrode Material Approach for the Analytical Sensing of pH"; ChemPhysChem 2004, 5, pp. 669 to 677.

(56) References Cited

OTHER PUBLICATIONS

Wildgoose et al: "Anthraquinone-derivatised carbon powder: reagentless voltammetric pH electrodes"; Talanta, 60 (2003) 887.
Williams J.M.: "Getting reliable On-Site H2S and CO2 Concentrations for anti-corrosion measures"; SPE paper 81495 (2003).
GB Search and Examination Report dated Sep. 25, 2008.
PCT Search Report and Written Opinion dated Sep. 3, 2009.
Shu et al., "Synthesis and Charge-Transport Properties of Polymers Derived from the Oxidation of 1-Hydro-1'-(6-(pyrrol-1-yl)hexyl)-4,4'-bipyridinium Bis(hexafluorophosphate) and Demonstration of a pH-Sensitive Microelectrochemical Transistor Derived from the Redox Properties of a Conventional Redox Center," J. Phys. Chem., 1988, vol. 92: pp. 5221-5229.
Smith et al., "pH Dependence of the Electrochemical Behavior of Surfaces Modified with a Polymer Derived from a Monomer Consisting of Two Viologen Subunits Linked by a Quinone: Evidence for 'Rectification' by Synthetic Molecular Materials," J. Am. Chem. Soc., 1986, vol. 108: pp. 3522-3525.

\* cited by examiner

ELECTROCHEMICAL SENSOR UTILISING A DUAL REDOX SYSTEM CONTAINED WITHIN A SINGLE MOLECULE

This invention relates to electrochemical sensors for determining constituents of fluids. Fields in which the invention may be utilised include, although are not restricted to, the analysis of water at the Earth's surface and also the analysis of a subterranean fluids which may be in an aquifer or downhole in a hydrocarbon reservoir.

BACKGROUND OF THE INVENTION

There are numerous circumstances in which it is desirable to detect, measure or monitor a constituent of a fluid. One of the commonest requirements is to determine hydrogen ion concentration (generally expressed on the logarithmic pH scale) of aqueous fluids which may for example be a water supply or an effluent. The determination of the pH of a solution is one of the most common analytical measurements and can be regarded as the most critical parameter in water chemistry. Nearly all water samples will have their pH tested at some point in their life cycle as many chemical processes are dependent on pH. Another common requirement is to determine oxygen content in water.

A particularly challenging context is the analysis of downhole fluids, which can be an important aspect of determining the quality and economic value of a hydrocarbon formation. Knowledge of downhole formation (produced) water chemistry can be applied to save costs and increase production at all stages of oil and gas exploration and production. Measurements obtained downhole can be important for a number of key processes of hydrocarbon production, including:

Prediction and assessment of mineral scale and corrosion;
Strategy for oil/water separation and water re-injection;
Understanding of reservoir compartmentalization/flow units;
Characterization of water break-through;
Derivation of the water cut $R_W$; and
Evaluation of downhole $H_2S$ partition in the oil and or water (if used for $H_2S$ measurements).

Some chemical species dissolved in water (for example, $Cl^-$ and $Na^+$) do not change their concentration when moved to the surface either as a part of a flow through a well, or as a sample taken downhole. Consequently information about their quantities may be obtained from downhole samples and in some cases surface samples of a flow. However, the state of chemical species, such as $H^+$ (pH=−log [concentration of $H^+$]), $CO_2$, or $H_2S$ may change significantly while tripping to the surface. The change occurs mainly due to a difference in temperature and pressure between downhole and surface environment. In case of samples taken downhole, this change may also happen due to degassing of a sample (seal failure), mineral precipitation in a sampling bottle, and (especially in case of $H_2S$)—a chemical reaction with the sampling chamber. It should be stressed that pH, $H_2S$, and $CO_2$ are among the most critical parameters for corrosion and scale assessment. Consequently it is of considerable importance to determine their downhole values and there have been proposals for analytical sensors to be used downhole.

One approach to measurements, both at the Earth's surface and downhole, involves a solid-state probe utilising redox chemistries at the surface of an electrode.

U.S. Pat. No. 5,223,117 disclosed a pH sensor in which two molecular species were attached to a gold substrate. This was used with a very much larger counter electrode. The species attached to the gold substrate were described as effectively providing two electrodes shorted together, whose potential relative to the counter electrode could be controlled. One of the attached species was ferrocene which served as reference electrode because it displays a redox potential which is generally insensitive to the concentration of hydrogen ions. The other was hydroquinone which served as an indicator electrode, with a redox potential that is dependent on hydrogen ion concentration. This sensor was used in voltammetry in which the gold substrate with the attached redox systems and the counter electrode are placed in contact with a solution to be tested. The potential applied to the gold substrate was systematically varied and current flow was monitored. A plot of current against applied voltage, a so-called voltammogram, shows current peaks when the redox reactions take place at specific values of applied voltage. The difference in voltage between the voltages giving peak current for the ferrocene reference and a peak current for hydroquinone provides a measure of the pH of the solution under test.

WO 2005/066618 disclosed a sensor in which two different pH sensitive molecular redox systems and a pH insensitive ferrocene reference were attached to the same substrate. One pH sensitive redox system was anthraquinone (AQ) and the second was either phenanthrenequinone (PAQ) or alternatively was N,N'-diphenyl-p-phenylenediamine (DPPD). Combining the responses of the two pH sensitive redox systems relative to the reference gave an increasing sensitivity to pH.

In both of the disclosures mentioned above the redox systems were mixed together and applied to the conductive substrate. Consequently the proportions of redox systems provided on the substrate were dependent on the proportions in the mixture and the efficacy of take-up onto the substrate.

WO 2007/034131 disclosed a sensor with two redox systems incorporated into a copolymer. The exemplified copolymer was made from vinyl ferrocene and vinyl anthracene so that the two redox systems were present as side chains from the hydrocarbon backbone of the polymer. This use of a polymeric species as active component of the electrode was stated to decrease instability in the electrode performance.

SUMMARY OF THE INVENTION

The present invention provides an electrochemical sensor comprising a solid, electrically conductive substrate, and a plurality of redox systems located on a surface of the substrate but which differ in sensitivity to the concentration of a species to be detected, wherein the plurality of redox systems are contained in the same chemical compound which is of determinate structure. For convenience this compound will be referred to below as a "multi-redox compound".

So in common with the earlier disclosures above, there is more than one redox system attached to the substrate of the sensor, but in this invention they are provided as part of a single molecule which has a determinate structure rather than being provided separately on the substrate or provided as part of a copolymeric macromolecule which will not have a single determinate structure but rather will have variable and somewhat indeterminate length as a result of the polymerisation by which it is made. This avoids two problems which have been encountered when redox systems are provided on macromolecules. The vast majority of polymers have transition temperatures above which the physical properties of the polymer alter. There is a loss of physical stability, which can be profoundly detrimental to the ability of a polymer to act as a sensor. Secondly, when redox systems are distributed along a polymer chain, it is possible for an electron to hop from one redox centre to the next along the chain, interfering with reversibility of the redox reaction. This phenomenon has been demonstrated in particular for polyvinyl ferrocene and its derivatives, where it was found that the cyclic voltammetric response can be sensitive not only to the analyte of interest but also to the concentration of other anions in solution, with decays in signal observed in the presence of certain anions (see K. L. Robinson and N. S. Lawrence, Electrochem. Commun., vol 8 page 1005 (2006).

This multi-redox compound which is not a copolymer may be characterised by one or more of several features, as follows:

It is likely to be monomeric or dimeric. A trimeric structure can be envisaged but is likely to be less convenient. Thus it may be such as to contain no more than three repeats of any moiety in the structure. It is likely to have molecular weight below 1000, probably below 500.

If the compound is monomeric it may contain a single instance of each of the redox systems, although it would be feasible for a monomeric compound to contain one instance of one redox system and two or more of another. If the compound is dimeric it will likely contain two instances of each redox system, although two instances of one redox system and four of another would be possible. Whether the compound is monomeric, dimeric or trimeric, it may possibly be defined as containing at most three instances of each redox system.

The redox systems may be directly joined together in the compound through covalent bonds, or may be joined through a linking group to which they are both covalently joined.

We have found that when two redox systems are present in the same chemical compound (a multi-redox compound of this invention) it is possible for one redox system in the compound to be sensitive to the concentration of the species to be detected while another is essentially insensitive to the concentration of the same species and so can serve as a reference. This useful possibility may be facilitated if one redox system undergoes electrochemical oxidation from an equilibrium state of the compound while another redox system undergoes reduction from an equilibrium state of the molecule.

So it is preferred that one redox system displays a reversible reduction or oxidation at a voltage which is sensitive to the concentration of a species to be detected, and another redox system in the same molecule displays a reversible reduction or oxidation at a voltage which is essentially insensitive to the concentration of the said species to be detected. This may in particular arise if the electrochemical reaction of one of the redox systems involves the species to be detected whilst the second redox reaction does not involve the species to be detected. Potentiometric sensing may then be used to determine the respective voltages at which the two redox systems display their peak currents and hence measure the voltage difference which will vary with the concentration of the species to be detected.

It is also within the scope of this invention that two redox systems in the same multi-redox compound are both responsive to the concentration of a species to be detected, but differ in their responses, as for instance anthraquinone (AQ) and phenanthrenequinone (PAQ).

In this event a reference redox system which is essentially insensitive to the concentration of the species to be detected could be provided as a third redox system in the same multi-redox compound. Alternatively, but less preferably, a reference redox system could be applied separately to the substrate.

Significant embodiments of this invention are pH sensors, in which one redox system is essentially responsive to changes in hydrogen ion concentration while another redox system is essentially insensitive to hydrogen ion concentration and acts as a reference.

A preferred reference redox system is ferrocene which will be directly or indirectly chemically attached to another redox system and may also have other groups, such as substituent groups, attached to it. Other metallocenes and tetrasubstituted phenylene diamines are also essentially insensitive to pH and could be used as reference redox systems.

A redox system which is sensitive to hydrogen ion concentration is anthraquinone (AQ) as in the prior documents mentioned above. Other possible pH sensitive redox systems include other quinones such as benzoquinone or phenanthrenequinone, phenylene diamines, catachols and phenothiazinium dyes.

Redox systems used in accordance with this invention for measuring pH may also have application in detecting or measuring a second species of interest. This possibility arises if the electrochemical reaction of a redox system couples to a reaction of a second species of interest, so that the redox system acts as a catalyst for the reaction of the second species. This second species can be determined by means of an amperometric measurement to measure any increase in the electric current which flows and the magnitude of the increase in current provides a measure of the concentration of the second species.

More specifically, if oxygen is present in an aqueous electrolyte, the electrochemical reduction of a quinone can couple to the reduction of that oxygen to water. The quinone redox system then serves as a catalyst in the electrochemical reduction of oxygen and the concentration of oxygen can be determined from the increase in electric current compared with the current which flows in the absence of oxygen.

The reactions can be represented as:

$$AQ+2H_2O+2e^-\rightarrow AQH_2+2OH^-$$

$$AQH_2+\tfrac{1}{2}O_2\rightarrow AQ+H_2O$$

Under alkaline conditions, oxygen can be converted to hydrogen peroxide, the second step of the above reaction scheme then taking the form:

$$AQH_2+O_2\rightarrow AQ+H_2O_2$$

If the electrochemical sensor is in contact with a non-aqueous liquid such as acetonitrile, the electrochemical reduction of a quinine can again couple to the reduction of oxygen, but the oxygen is reduced to superoxide, thus:

$$AQ+e^-\rightarrow AQ^{\cdot-}$$

$$AQ^{\cdot-}+O_2\rightarrow AQ+O_2^{\cdot-}$$

The redox reaction of ferrocene can couple to the oxidation of hydrogen sulphide to sulphur, so that the concentration of hydrogen sulphide can be determined from the increase in current compared to the current which flows in the absence of hydrogen sulphide. The reactions can be written as In a development of this invention, one redox system can be provided as a nitro-substituted aromatic moiety. By application of sufficient voltage some of the nitro groups can be irreversibly reduced electrochemically to nitroso groups and the nitroso-substituted aromatic moiety then displays a pH sensitive reversible redox conversion to the corresponding hydroxylamino-substituted moiety In the event that this nitroso-/hydroxylamino-substituted moiety becomes depleted while some of its nitro substituted precursor remains available, a voltage pulse can be applied to reduce some more of the nitro-substituted precursor.

A nitrosubstituted aromatic moiety can be provided as a nitrophenyl substituent on ferrocene, obtained through reaction of a nitrophenyl diazonium salt with ferrocene. Other nitro-substituted compounds are available and can be used similarly, for example an orthomethoxy paranitrophenyl diazonium salt is available as Fast Red A and 2,5-dimethoxy-4-([4-nitrophenyl]azo)benzenediazonium chloride, stabilised with zinc chloride, is available as fast black K.

The substrate which carries the compound containing the plurality of redox systems should of course be electrically conductive but should not be chemically degraded by exposure to the fluid to which it is exposed. Noble metals have traditionally been used for electrodes, and may possibly be used in this invention, especially if the sensor is to be used to measure pH in a context where hydrogen sulfide is absent. However, in some embodiments of this invention the substrate is provided by elemental carbon, which is not susceptible to attack by sulfides or thiol groups.

The most common forms of conducting carbon used in electrode manufacture are glassy carbon, carbon fibres, carbon black, various forms of graphite, carbon paste, boron doped diamond and carbon epoxy. One further form of carbon, which has seen a large expansion in its use in the field of electrochemistry since its discovery in 1991 is the carbon nanotube (CNT). The structure of CNTs approximates to rolled-up sheets of graphite and can be formed as either single or multi-walled tubes. Single-walled carbon nanotubes (SWCNTs) constitute a single, hollow graphite tube. Multi-walled carbon nanotubes (MWCNTs) on the other hand consist of several concentric tubes fitted one inside the other.

The multi-redox compound which contains the plurality of redox systems may be chemically bound to the substrate. Chemical reactions capable of binding a molecule to a substrate are known. For instance U.S. Pat. No. 5,223,117 made use of the reaction of a thiol group with a gold substrate.

The derivatisation procedures available for attaching to a carbon substrate encompass two main strategies of reaction. The most common involves electrochemical induced derivatisation leading to the formation of a covalent bond between a carbon electrode and the functional group. Examples have included:

electro-oxidation of alcohols—see B. Gou, J. Anzai and T. Osa, Chem. Pharm. Bull., vol 44, page 860 (1996);

electro-oxidation of primary and secondary amines—see See B. Barbier, J. Pinson, G. Desarmot and M. Sanchez, J. Electrochem. Soc., vol 137, page 135. (1990) and S. Antoniadou, A. D. Jannaloudis, P. D. Jannadoukakis and E. Theodoriu, J. Appl. Electrochem., 1992, vol 22, page 1060 (1992);

electro-oxidation of carboxylates—see C. P. Andrieux, F. Gonzalez and J. M. Saveant, J. Am. Chem. Soc., vol 119, page 4292 (1997);

electro-oxidation of hydrazides—see M. A. Hayes and W. G. Kuhr, Anal. Chem., vol 71, page 1720 (1999); and electro-reduction of diazonium salts—see P. Allongue, M. Delamer, B. Desbat, O. Fagebaume, R. Hitmi, J. Pinson and J. M. Saveant, J. Am. Chem. Soc., vol 119, page 201 (1997).

A second and more general strategy for binding to a carbon substrate involves a homogeneous derivatisation procedure. This has focused on the oxidation of the carbon surface by a homogeneous oxidising agent such as potassium permanganate or nitric acid, which has an analogous effect to direct electrochemical oxidation by providing oxygenated functional groups on the carbon surface, which can then be chemically reacted with various moieties to functionalise the carbon. Another approach is the homogeneous reduction of diazonium compounds in reducing media—see M Pandurangappa, N. S. Lawrence, R. G. Compton, Analyst, vol 127, page 1568 (2002). WO2005/066618 describes the diazocoupling of anthraquinonyl and nitrophenyl groups onto carbon nanotubes by means of the reduction of diazonium salts.

A further possibility is that the multi-redox compound may be immobilised onto the substrate by deposition from a solution in a volatile solvent which is allowed to evaporate, or by a mechanical action, such as rubbing it onto a surface of the substrate.

The substrate, bearing the multi-redox compound which contains the plurality of redox systems, may be in direct contact with the fluid to be tested especially when that fluid is water. Another possibility is that a semi-permeable membrane is used to separate the fluid being tested from the substrate. In this case, the substrate would be in direct contact with an electrolyte and the membrane would separate this electrolyte from the fluid to be tested.

This invention may be employed in a diverse range of applications, including equipment for testing aqueous fluids at the Earth's surface. However, an area of application which is of particular interest to us is in devices for testing subterranean fluids, in particular devices to be used downhole in a well.

Downhole measurement tools for oilfield applications are known as such. An electro-chemical technique using a sensor in accordance with the present invention can be applied for example as part of a production logging tool or an open hole formation tester tool for use in a well drilled for oil or gas. In such a case, the invention may be used in providing a downhole real-time water sample validation or downhole pH or sulfide measurement which in turn can be Used for predicting mineral scale and for corrosion assessment. Such tools may be devices lowered into a well by means of a cable, such as wireline or slickline, or may be tools carried into a well by coiled tubing, or even tools which are positioned downhole for a longer period.

Downhole measurement tools are also used in wells drilled to monitor groundwater or to access subterranean aquifers. A sensor in accordance with the invention can be utilised in such tools, notably in providing real time measurement of pH and/or oxygen content.

These and other features of the invention, preferred embodiments and variants thereof, possible applications and advantages will become appreciated and understood by those skilled in the art from the following detailed description and drawings.

DETAILED DESCRIPTION

The methods and apparatus of the present invention are based on the measurement of the electromotive force (e.m.f.) or potential E in a potentiometric cell which includes measuring and reference electrodes (half-cells). The theory of voltammetry and its application to measurements are both well developed. The subject is discussed in WO 2005/066618 above and is covered in standard textbooks, such as A J Bard and L Faulkner "Electrochemical Methods: Fundamentals and Applications" ($2^{nd}$ ed 2001).

Figure 1:
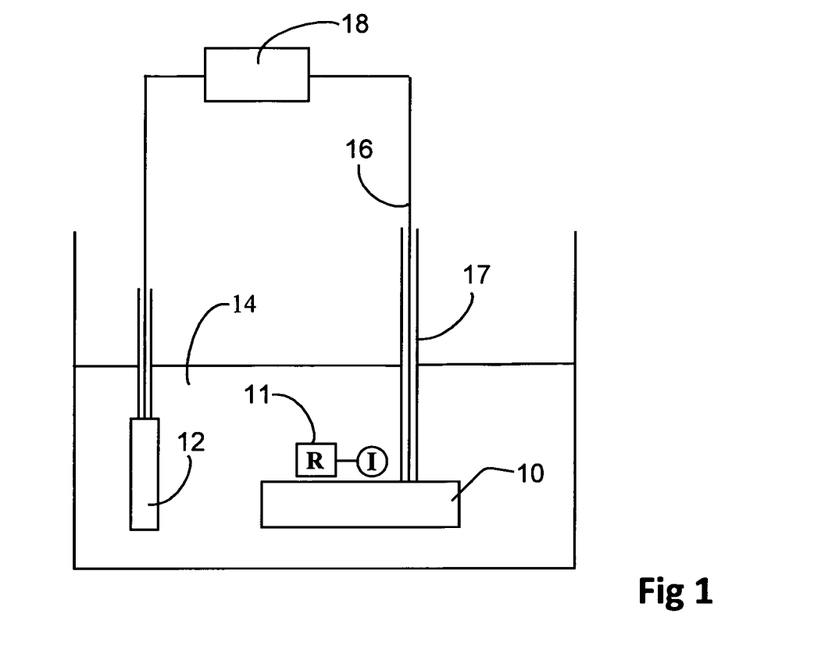
FIG. 1 diagrammatically illustrates an embodiment of the invention in a potentiometric cell.

As shown in FIG. 1, a pH sensor is an electrode with a substrate 10. Immobilised on this substrate is a multi-redox compound II in which each molecule contains a reference redox system R and a second redox system I. This pH sensor electrode and a counter electrode 12 are placed in contact with a test solution 14, thus forming a potentiometric cell. Both of them are joined by electrical connections 16 (running within insulation 17 so that they are not in contact with the test solution) to a potentiostat 18 which is able to apply a variable potential difference between the substrate 10 and the counter electrode 12. The potentiostat 18 is used to carry out voltammetry experiments, measuring and recording the current which flows as the applied voltage is varied. Suitable potentiostats are available from Eco Chemie BV, Utrecht, Netherlands.

In a traditional potentiometric cell there would be a counter electrode, a reference electrode and a separate measuring electrode. Here the substrate 10 and the reference redox system R of the molecules immobilised on it can be regarded as performing the role of a reference electrode, while the substrate 10 and the other redox system I of the molecules immobilised on it perform the role of the measuring electrode, with the reference and measuring electrodes directly connected together, because the substrate 10 is common to both.

Example 1

In this example the redox systems are ferrocene and anthraquinone, in a compound which is anthraquinonyl ferrocene (alternatively named ferrocenyl anthraquinone) denoted here as Aq-Fc. This compound has been reported in the literature: see Roberts R M G Journal of Organometallic Chemistry vol 388 page 181 (1990) which gives a preparation procedure and properties of the compound.

A similar preparation procedure was used here: to a solution of ferrocene (1 g, 4.23 mmol) in dry diethyl ether (30 ml) was added portionwise Fast Red AL Salt, which is anthraquinone-1-diazonium chloride (1.2 g, 4.43 mmol). The solution was stirred under a nitrogen atmosphere for 48 hours at ambient temperature of 20-25° C. Water (50 ml) was added to this solution and the organic phase was separated and dried over dry MgSO4. The solvent was then evaporated under vacuum and the residue was purified on a basic alumina chromatography column using a gradient of light alkanes (boiling range 40-60° C.) and diethyl ether as eluent to give the desired compound (Aq-Fc) in 30% yield.

Figure 2:
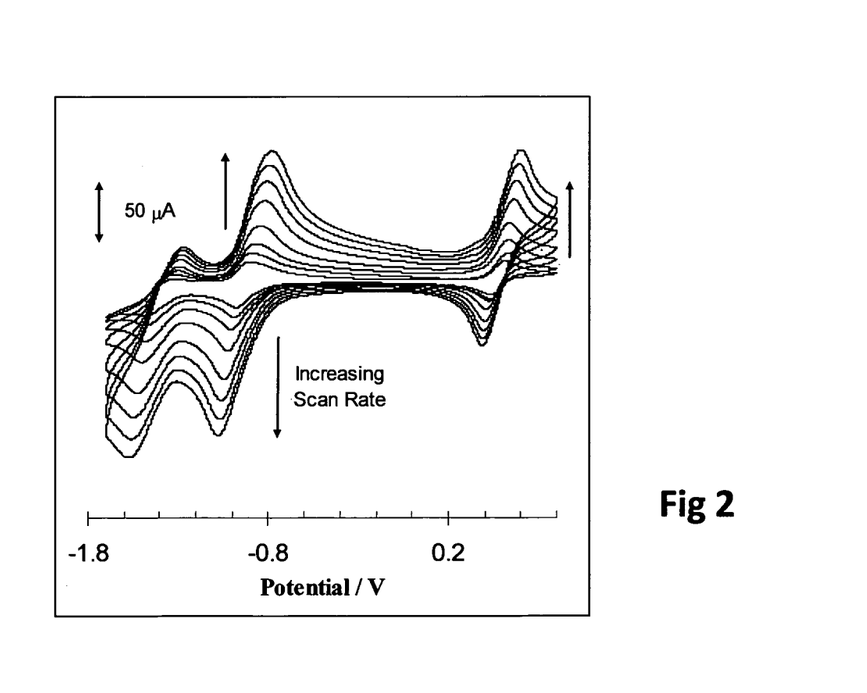
FIG. 2 shows the cyclic voltammetric signal, at several scan rates, of 1 mM Aq-Fc dissolved in acetonitrile containing 0.1 M tetrabutyllammonium hexafluorophosphate.
Figure 3:
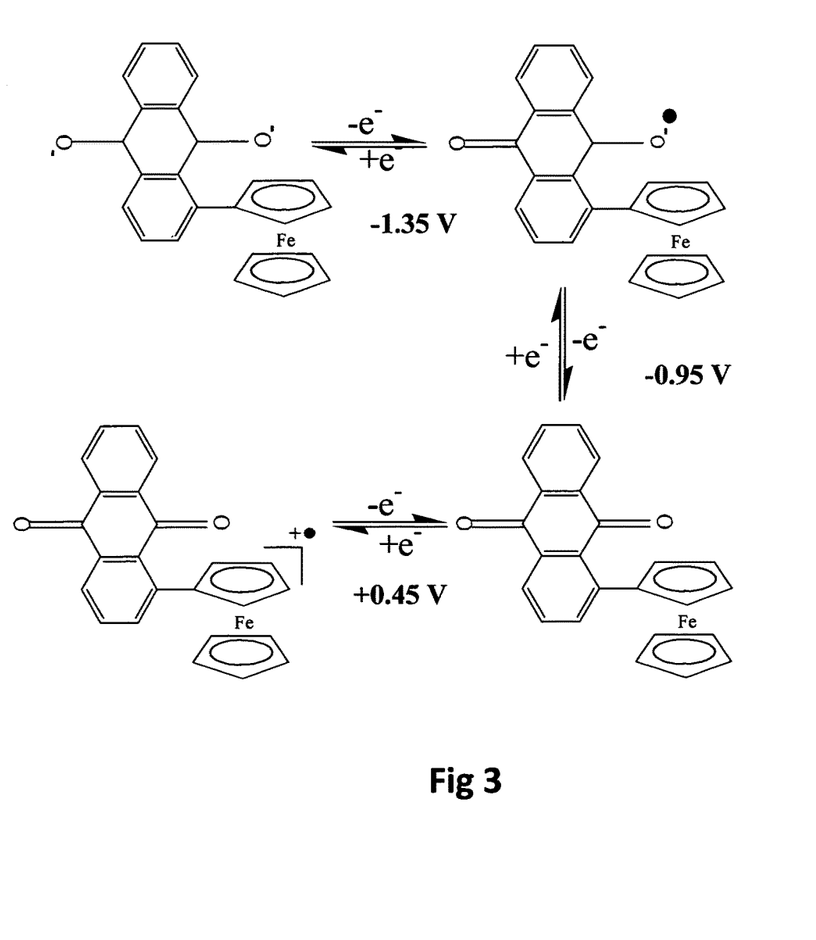
FIG. 3 illustrates the redox chemistry of the Aq-Fc species in acetonitrile.

Electrochemical characterization of the anthraquinonyl ferrocene was first conducted in a non-aqueous medium. A degassed solution was prepared, containing 1 mM Aq-Fc in acetonitrile which also contained 0.1 M tetrabutylammonium hexafluorophosphate. A conventional cyclic voltammetry experiment was carried out, using a glassy carbon working electrode (3 mm diameter, Bioanalytical Systems, Kenilworth, UK) a silver wire reference electrode and a platinum wire counter electrode The potential relative to the counter electrode was first started at 0.0V, cycled to +0.7 V, then reversed to −1.2 V before returning to the start potential of 0.0V. The scan rate was varied from 0.025 to 1 Volt·sec-1. The resulting voltammogram (plot of current against potential) is shown as FIG. 2. Three reversible redox couples at +0.45 V, −0.95 V and −1.35 V, can be clearly observed at each scan rate studied. The redox couple at +0.45 V can be attributed to the single electron oxidation and reduction of the ferrocene moiety whilst the couples at −0.95 V and −1.35 V can be attributed to the redox behaviour of the anthraquinone moiety which undergoes two one electron reductions in non aqueous media, forming the corresponding hydroquinone di-anion species. FIG. 3 summarizes the various electrochemical pathways. These results confirm the presence of both the anthraquinone and ferrocene moieties on the synthesized molecule. Plots of peak current as a function of square root of scan rate were found to be linear for each redox process consistent with the Aq-Fc species undergoing as solution/diffusion based redox process.

Voltammetry of the Aq-Fc species was next studied in aqueous solution. For this, some of the Aq-Fc compound was immobilized on the surface of a glassy carbon electrode. A 1 mg/mL solution of Aq-Fc was prepared in dichloromethane and a 20 µL aliquot of this solution was placed dropwise onto the surface of the glassy carbon electrode and allowed to dry, leaving a residue of Aq-Fc immobilized on the electrode surface.

Figure 4:
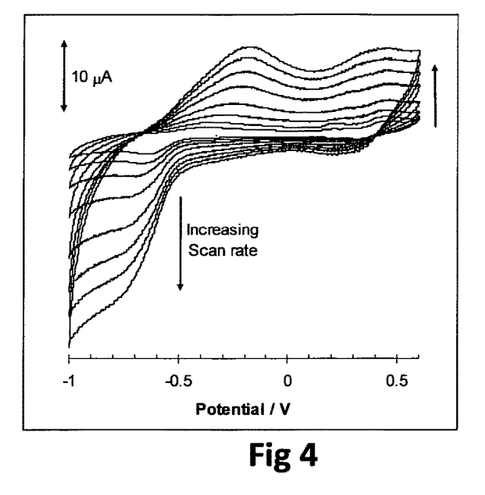
FIG. 4 shows the cyclic voltammetric signal, at several scan rates, of Aq-Fc immobilized on an electrode when placed in pH 7 buffer solution.

The electrode which had been prepared in this way was then placed into pH 7 phosphate buffer. Cyclic voltammetry was carried out at several scan rates in the range from 0.025 to 1 Volt·sec$^{-1}$. A platinum wire and a saturated calomel reference electrode (Radiometer, Copenhagen) completed the cell assembly. FIG. 4 shows the cyclic voltammetric response which contains current peaks associated with the anthraquinone and ferrocene moieties. In this case the ferrocene moiety undergoes a 1 electron oxidation and the anthraquinone species undergoes a 2 proton, 2 electron reduction to the corresponding hydroquinone species.

Figure 5:
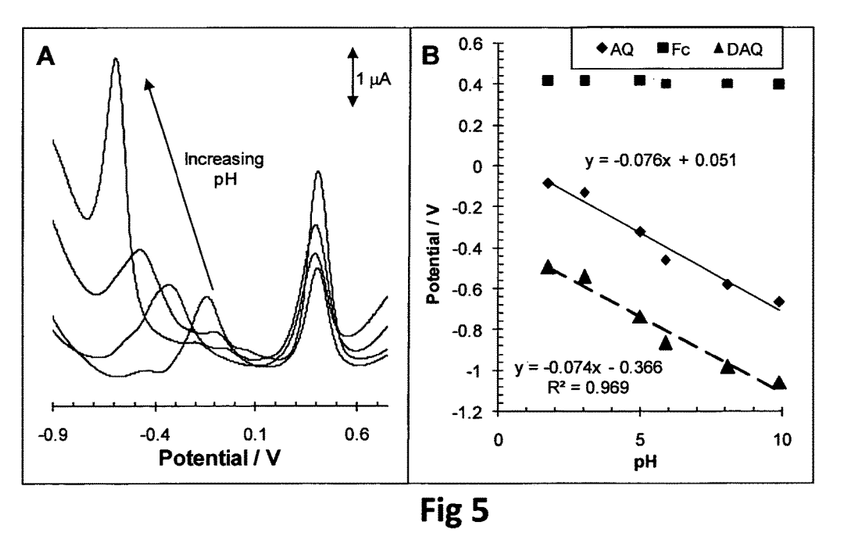
FIG. 5A shows the square wave voltammetric response of Aq-Fc immobilized on an electrode when placed in buffer solutions of pH 3, 5, 5.9 and 8.
FIG. 5B shows plots of peak potential against pH for the Fc species and the AQ species, and also shows the difference (DAQ) in redox potential between the two species at each pH studied.

Use as a pH sensor was next demonstrated by placing the electrode in various pH buffer solutions (pH range 3-8) and carrying out voltammetry. The square wave voltammetric response of the Aq-Fc immobilized layer at four values of pH is shown in FIG. 5A. Two voltammetric waves are clearly seen in each case; the first is at lower potentials and has a pH dependent redox potential and the second has a peak at +0.41 V which is pH independent. This is consistent with the data detailed in FIG. 4.

FIG. 5B is a graph of the variation in peak potential of both the anthraquinone and ferrocene species, along with the difference in peak potential against pH.

These results in FIGS. 5A and 5B show that the current peak for ferrocene occurs at a voltage which is effectively independent of pH, whilst that for anthraquinone varies with pH. The plot detailing the difference in redox potential of the two species is linear over the entire pH range. Analysis of the slope provides a value of 74 mV/pH unit.

Figure 6:
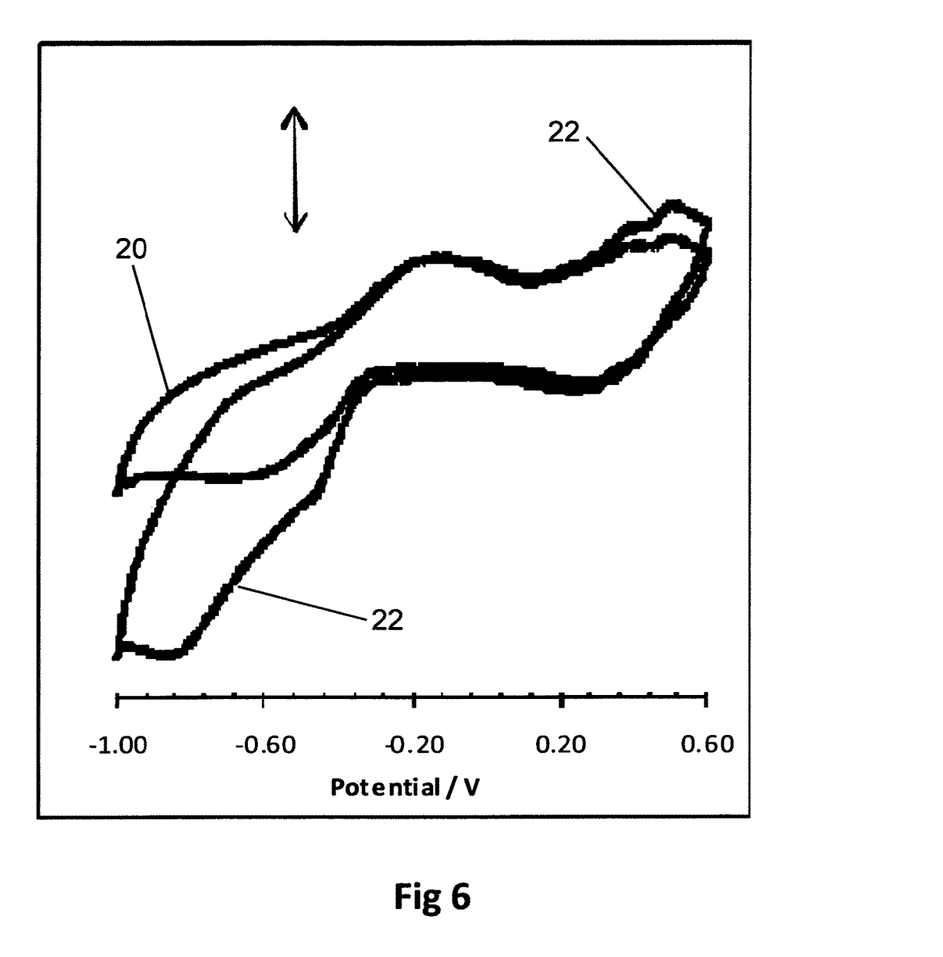
FIG. 6 shows superimposed the cyclic voltammetric signals of Aq-Fc immobilized on an electrode when placed in pH 4 buffer solution, in the presence and absence of oxygen.

A further voltammetric experiment demonstrated the ability of the Aq-Fc to take-on a dual sensor role. FIG. 6 shows the voltammetric response of the glassy carbon electrode with Aq-Fc compound immobilized thereon when placed in pH 9 buffer solution in the presence and absence of oxygen. The scan rate was 0.1 Volt·sec$^{-1}$. The curve in the absence of oxygen is indicated by reference numeral 20 and in the presence of oxygen by reference numeral 22. The double headed vertical arrow indicates 5 microamps on the vertical scale. It can be clearly seen that the reductive peak at -0.7 to -1.0 volts displays a considerable increase in current in the presence of oxygen. This is consistent with the anthraquinone moiety electrocatalysing the reduction of oxygen. Such an electrocatalytic reaction could be utilized in the quantitative determination of oxygen. The ferrocene moiety does not participate in this electrocatalysis, but continues to provide a reference value.

Example 2

In this example the redox systems are ferrocene and hydroxylaminobenzene, in a single multi-redox compound which is hydroxylaminophenyl ferrocene. This compound is believed to be novel.

To a solution of ferrocene (2 g, 10 mmol) in dry diethyl ether (50 ml) was added slowly nitrobenzene diazonium tetrafluoroborate (3.55 g, 15 mmol) under a flux of nitrogen. The solution was stirred at room temperature for 16 h. Water was added to the solution and the ether phase was separated and washed with water and brine (50 ml). The organic phase was then dried over magnesium sulfate and the solvent evaporated under vacuum. The residue was the purified on a basic alumina chromatography column using a gradient of light alkanes (boiling range 40-60° C.) and diethyl ether as eluent to give the desired compound p-nitrophenyl ferrocene:

This product was obtained as a purple solid in 35% yield.

The compound was examined by nmr and the following peaks were observed:

1H NMR (400 MHz, CDCl3) δ 8.13 (2H, d, J=8.5 Hz, o-H—ArNO2), 7.55 (2H, d, J 8.5 Hz, m-H—ArNO2), 4.73 (2H, t, o-H-Cp-Ar), 4.46 (2H, t, m-H-Cp-Ar), 4.04 (5H, s, H-Cp');

13C NMR (100 MHz, CDCl$_3$) δ 148.2 (C—NO2), 145.3 (C—Ar), 125.8 (m C—ArNO2), 123.8 (o-C—ArNO2), 81.7 (ipso C-Cp), 70.6 (m-CH-Cp-Ar), 70.0 (CH-Cp'), 67.2 (o-C-Cp-Ar)

Some of this p-nitrophenyl ferrocene was immobilized on a glassy carbon electrode as in the previous example. Cyclic voltammetry was carried out with the electrode placed in pH7 phosphate buffer, using a platinum wire counter electrode. The potential was first started at 0.0 V, swept to +0.6 V, reversed and swept back to -0.8 V before returning to 0.0 V (scan rate was 0.1 Volt·sec-1).

Figure 7:
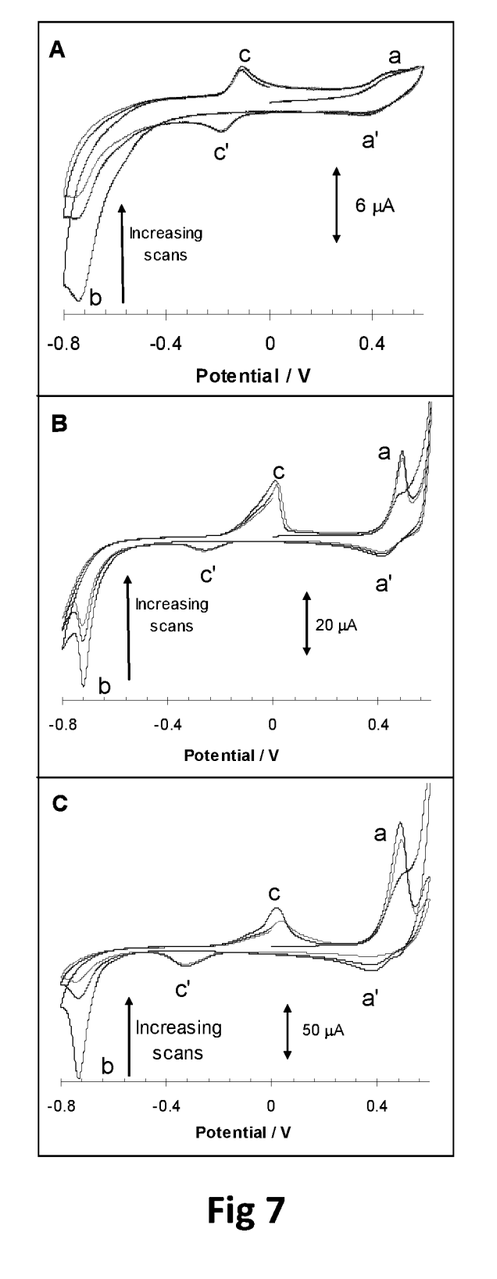
FIG. 7A shows the voltammetric response of nitrophenylferrocene immobilized on an electrode when placed in pH 7 buffer solution.
FIGS. 7B and 7C show the corresponding voltammetric responses with p-nitrophenyl t-butylferrocene and p-nitrophenyl diethylferrocene respectively.

FIG. 7A shows three successive scans. On the initial oxidative sweep, a single oxidation wave is observed at +0.49 V (a), upon reversal of the scan direction two reduction waves are observed at +0.37 V (a') and -0.75 V (b). Finally an oxidation wave at -0.08 V (c) is observed when the potential was swept back to 0.0 V. Upon repetitive scanning it can be seen that a new reduction at -0.24 V (c') emerges which is associated with the new oxidative wave at -0.08 V (c), furthermore the reduction wave at -0.75 V (b) decays in magnitude.

Figure 8:
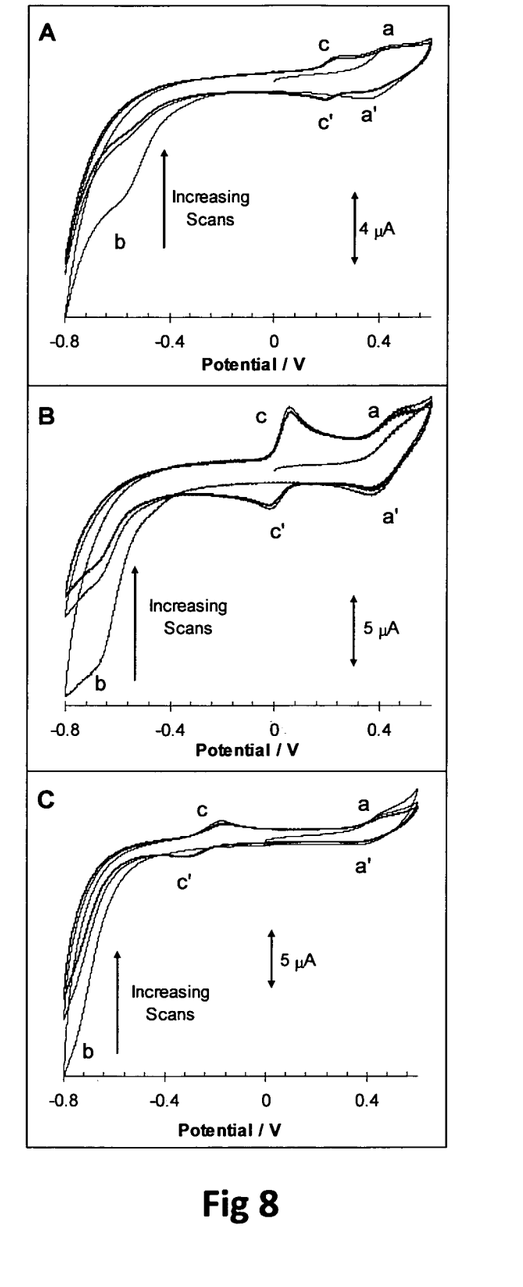
FIG. 8 shows the voltammetric responses of nitrophenylferrocene immobilized on an electrode when placed in solutions at pH 1, 4 and 9.

The above experiment was repeated, using three solutions of different pH. The results are shown in FIG. 8. The solutions were 0.1 M HCl (FIG. 8A) pH 4 buffer (FIG. 8B) and pH 9 buffer (FIG. 8C). A comparison of each voltammogram with that detailed in FIG. 7A (pH 7 buffer), reveals that the voltammetric profiles have some features in common. The first oxidative sweep produces a single oxidation wave at +0.49 V (a) with a corresponding reduction wave at +0.37 V, lowering the potential further on the first sweep reveals the presence of a second reduction wave (b) in the region from -0.6 to -0.8 volts. Upon further voltammetric cycling new oxidative and reductive waves (c and c') are observed and the reductive wave (b) diminishes.

The pH invariant redox couple (a,a') is attributed to the reversible oxidation and reduction of the ferrocene moiety. The reduction wave (b) is attributed to the irreversible reduction of the nitro group to a nitroso group as shown in the reaction scheme FIG. 9. The redox couple (c,c') which emerged is attributed to the reversible conversion of the nitroso group to a hydroxylamino group. As is apparent from FIG. 8, the potentials at which this reduction and oxidation occur change considerably with pH. It can be seen for instance that the oxidation potential (c) is +0.25V at pH1, +0.10V at pH 4 and −0.16V at pH 9. When the potentials at which there is peak current for the redox couple (c,c') were plotted against pH, they were found to vary linearly with pH.

Figure 9:
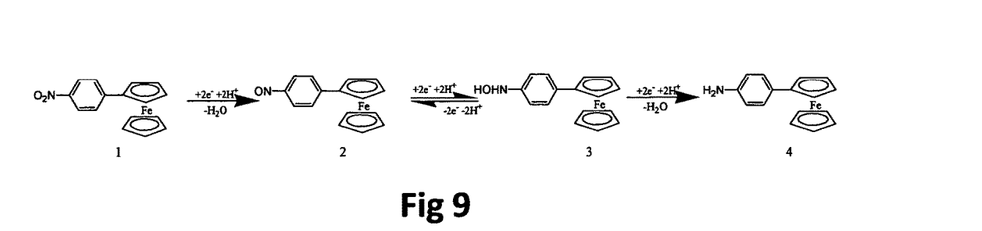
FIG. 9 is a reaction scheme showing the reduction of nitrophenylferrocene.

The further reduction of hydroxylamino to amino, as shown at the right hand side of FIG. 9 is suggested by literature on the electrochemical reduction of nitrogroups but was not observable in this experiment, in which the interconversion between nitroso and hydroxylamino was predominant.

Example 3 p-nitrophenyl t-butylferrocene (which is believed to be novel) was made from t-butylferrocene by the same procedure as in Example 2. The product was a mixture of two isomers:

As shown by the structures represented above, in one isomer, designated β, the p-nitrophenyl and t-butyl groups were on the same cyclopentadienyl ring of ferrocene. In the other isomer, which designated the 1' isomer and which was present in a greater amount, they were on different rings. The mixture was a purple solid and the two isomers could not be separated by column chromatography. Examination by nmr led to observation of the following peaks:

1H NMR. (400 MHz, CDCl$_3$) δ 8.13 (2H, d, J=8.50 Hz, o-H—ArNO$_2$), 7.55 (2H, d, J=8.50 Hz, m-H—ArNO$_2$), isomer β: δ 4.68 (1H, m, H-Cp), 4.64 (1H, m, H-Cp), 4.36 (1H, m, Cp), 4.01 (5H, m, H-Cp'), 1.28 (CCH$_3$);

isomer 1': δ 4.73 (o-H-Cp-Ar), 4.47 (m-H-Cp-Ar), 3.91 (H-Cp'); 3.88 (H-cp'), 1.16 (CCH$_3$);

13C NMR (100 MHz, CDCl$_3$)

isomer β: δ 148.9 (C—NO$_2$), 145.3 (C—Ar), 125.8 (o-C—Ar), 123.8 (m, C—Ar), 104.96 (C-Cp-C(CH$_3$)$_3$), 80.2 (C-Cp-Ar), 70.4 (C-Cp'), 67.7 (C-Cp), 65.9 (C-Cp), 64.6 (C-Cp), 31.4 (CH$_3$), 30.3 (C(CH$_3$)$_3$);

isomer 1': δ 148.3 (C—NO$_2$), 145.4 (C—Ar), 125.9 (o-C—Ar), 123:8 (m, C—Ar), 103.5 (C-cp-C(CH$_3$)$_3$), 81.4 (C-Cp-Ar), 71.2 (m-C-Cp-Ar), 69.66 (C-Cp'), 67.4 (o-C-Cp-Ar), 67.0 (C-Cp'), 31.4 (CH$_3$), 30.4 (C(CH$_3$)$_3$);

Some of this product was immobilized on a glassy carbon electrode and voltammetry in a pH7 buffer was carried out as in Example 2. The results are shown in FIG. 7B and are generally similar to those in FIG. 7A.

The procedure of this example was repeated using an o-methoxy p-nitro benzene diazonium salt to make the corresponding compounds with an o-methoxy substituent. Again some of the product was immobilized on a glassy carbon electrode and similar voltammetry results were obtained.

Example 4 p-nitrophenyl diethylferrocene was made from diethylferrocene by the same procedure as in Example 2. The product was a mixture of two isomers:

In the α isomer, but not the β isomer the p-nitrophenyl group and an ethyl group were on adjoining carbon atoms of a cyclopentadienyl ring. Once again these isomers could not be separated. Examination by nmr led to observation of the following peaks:

1H NMR (400 MHz, CDCl$_3$)

isomer α: δ 8.15 (2H, d, J 8.7, o-H—Ar—NO$_2$), 7.65 ((2H, d, J 8.7, m-H—Ar—NO$_2$), 4.44 (1H, m, H-Cp, CH—C-Ph), 4.28 (1H, m, H-Cp, CH—C-Et), 4.25 (1H, m, H-Cp, CHCHC-Et), 3.96 (2H, m, CH-Cp'), (3.90 (2H, m, CH-Cp'), 2.61 (2H, q, J=7.2 Hz, Cp-CH$_2$CH$_3$), 2.23 (2H, q, J=7.2 Hz, Cp'-CH$_2$CH$_3$), 1.21 (3H, m, CpCH$_2$CH$_3$), 1.07 (3H, t, J=7.2 Hz, CpCH$_2$CH$_3$);

isomer β: δ 8.12 (2H, d, J 8.7, o-H—Ar—NO$_2$), 7.49 (2H, d, J 8.7, m-H—Ar—NO$_2$), 4.6 (2H, m, H-Cp, CH—C—Ar), 4.34 (1H, m, H-Cp, CH—C-Et), 3.95 (1H, m, H-Cp'), 3.83 (2H, m, H-Cp'), 3.79 (2H, m, H-Cp'), 2.42 (2H, q, J=7.2 Hz, CH$_2$CH$_3$-Cp), 2.07 (2H, q, J=7.2 Hz, CH$_2$CH$_3$, Cp'), 1.21 (3H, m, CH$_2$CH$_3$-Cp'), 1.02 (3H, t, J=7.2 Hz, CpCH$_2$CH$_3$);

$^{13}$C NMR (100 MHz, CDCl$_3$)

isomer α: δ 148.5 (C—NO$_2$), 145.4 (C—Ar), 128.7 (m-C—ArNO$_2$), 123.3 (o-C—ArNO$_2$), 91.8 (C-Et-Cp'), 89.6 (C-Et-Cp), 82.6 (C—Ar—Cp), 70.7 (CH—C-Et-Cp), 70.2 (CH-Cp'), 69.7 (CH—C—Ar—Cp), 69.4 (CH-Cp'), 68.6 (CH—CHC-Et-Cp), 21.7 (CH$_2$-Cp), 21.6 (CH$_2$-Cp'), 14.9 (CH$_3$), 14.8 (CH$_3$);

isomer β: δ 148.7 (C—NO$_2$), 145.1 (C—Ar), 125.5 (m-C—ArNO$_2$), 123.1 (o-C—ArNO$_2$), 94.0 (C-Et-Cp), 92.3 (C-Et-Cp'), 80.5 (C—Ar—Cp), 70.7 (CH-Cp), 69.3 (CH-Cp'), 67.1 (CH-Cp), 66.7 (CH-Cp), 70.0 (CH-Cp'), 70.1 (CH-Cp'), 22.3 (CH$_2$-Cp'), 21.3 (CH$_2$—Cp), 14.9 (CH$_3$—Cp&Cp')

Some of this product was immobilized on a glassy carbon electrode and voltammetry in a pH7 buffer was carried out as in Example 2. The results are shown in FIG. 7C and are generally similar to those in FIGS. 7A and 7B.

Example 5

A layer of p-nitrophenylferrocene was immobilized on a glassy carbon electrode in the same manner as in previous examples. The electrode was then placed in pH7 buffer and its potential, relative to a relative to a saturated calomel reference electrode was cycled 10 times between +0.6 and −0.8 V to reduce nitro groups to hydroxylamino groups.

Figure 10:
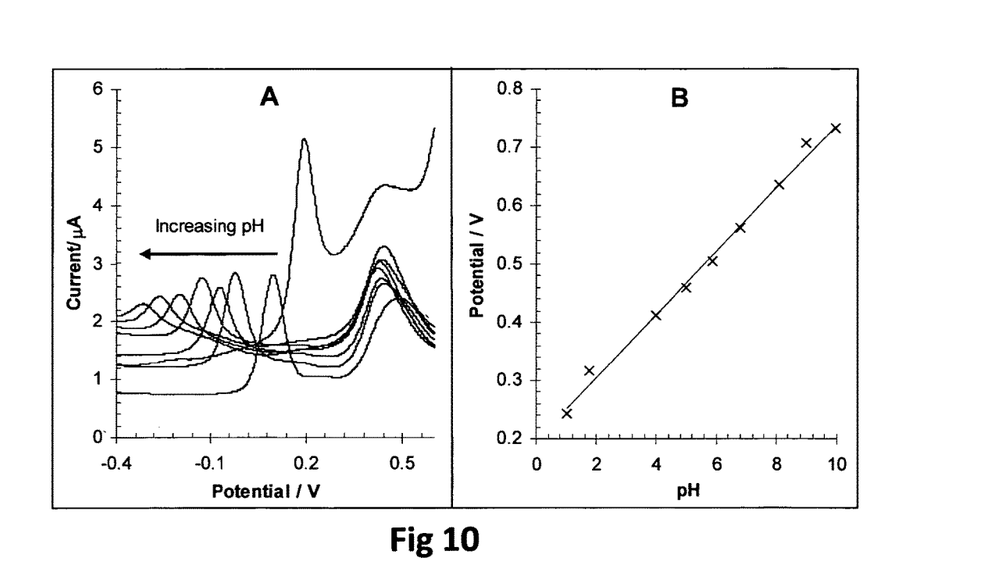
FIG. 10A shows the square wave voltammetric response of a pH sensor which has p-nitrophenylferrocene immobilized on an electrode and placed in buffer solutions of pH 1.0, 2.0, 5.0, 5.9, 7.0, 8.1, 9.0 and 9.9.
FIG. 10B is a plot of the difference in peak potential for the hydroxylaminophenyl and ferrocene moieties, against pH.

After this pre-treatment the electrode was used as a calibration-free pH sensor. The electrode was placed in buffer solutions of pH 1.0, 2.0, 5.0, 5.9, 7.0, 8.1, 9.0 and 9.9 at ambient temperature of 22° C. and the square wave voltammetric response was recorded. The corresponding responses are depicted in FIG. 10A. At each pH value studied two voltammetric waves were observed, the first at lower potentials was pH sensitive whilst the second at +0.45 V was pH independent. These waves can be attributed respectively to the oxidation of the hydroxylamine to the nitroso moiety and the oxidation of ferrocene to the corresponding ferricenium radical cation species. The corresponding plot of the variation in the hydroxylamine peak potential, with respect to ferrocene peak potential, as a function of pH is shown in FIG. 10B. This shows a linear response over the entire pH range studied (1-10), with a slope of 54.2 mV/pH unit. This is in reasonable agreement with the Nernstian predicted slope of 59.9 mV/pH unit.

This novel pH sensor was used to determine the pH of a river water sample. A value of 7.88 was obtained which is close to the value of 7.98 recorded using a commercially available pH probe.

The square wave voltammetric response of the novel pH sensor was also recorded over the pH range 4-9 at various temperatures in the range from 40 to 70° C. At each value of pH and temperature two oxidative waves were observed, similarly to the results above at ambient temperature. Plots of the variation in the hydroxylamine peak potential, with respect to ferrocene peak potential, as a function of pH, showed a slight increase in slope with temperature, consistently with Nernstian prediction, as set out in the following table:

| Temperature | Experimental mV per pH unit | Theoretical mV per pH unit |
|---|---|---|
| 298° C. | 54.2 | 59.9 |
| 313° C. | 59.3 | 62.1 |
| 323° C. | 62.1 | 64.1 |
| 333° C. | 63.3 | 66.1 |

The above experimental procedure, at ambient temperature was repeated using the p-nitrophenyl compounds of Examples 3 and 4. Analogous results were obtained.

Figure 11:
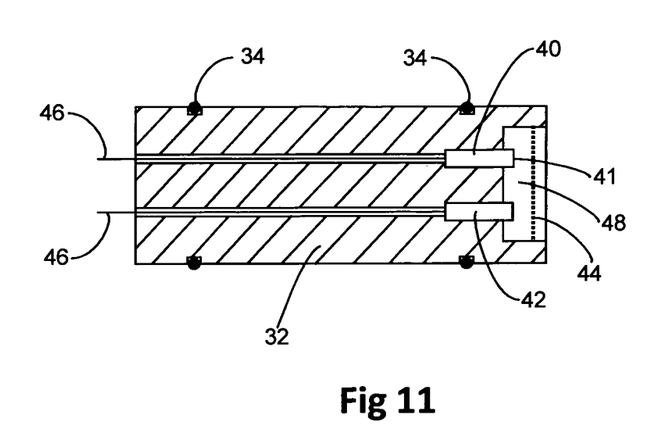
FIG. 11 is a diagrammatic cross section of a sensor unit embodying the invention.

FIG. 11 illustrates in cross section a sensor unit embodying the invention. It has a main body 32 which is cylindrical. This body is intended to be accommodated inside a cylindrical cavity in a wellbore tool or other structure and is encircled by two sealing rings 34 to provide a seal between the body 32 and the cavity accommodating it. The body 32 supports an electrode substrate 40, and a counter electrode 42. Electrical connections to the electrodes are indicated at 46. Immobilised on surface 41 of substrate 40 is a chemical compound ## of determinate structure which incorporates two redox systems as called for by this invention. This surface 41 and an end portion of the counter electrode 42 are in contact with an electrolyte retained by a membrane 44 within a cavity 48 at the end 49 of the body 32. This membrane 44 separates the electrolyte from the fluid under test, but is permeable to the species such as hydrogen ($H^+$) ions and bisulfide ($HS^-$) whose concentration is to be measured. Depending on the nature of the fluid under test, it may be possible to dispense with the membrane 44 and allow the surface 41 and counter electrode 42 to contact the test fluid directly.

Figure 12:
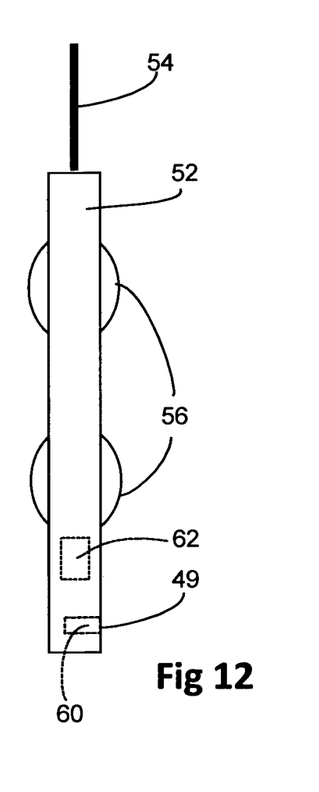
FIG. 12 is a diagrammatic illustration of a wireline tool incorporating the sensor unit of FIG. 11.

FIG. 12 diagrammatically illustrates a wireline tool with a generally cylindrical body 52 suspended at the lower end of a wireline 54. The body 52 is provided with centralisers 56 for positioning it within a wellbore. The body 52 may house a variety of devices for making measurements on the wellbore, the surrounding geological formation and on fluid within the wellbore. Amongst these is a sensor unit 60 such as that of FIG. 11. This is fitted into a cavity within the body 52 so that the end 49 of the sensor unit 60 is exposed to the fluid within the wellbore. The tool body 52 also encloses a unit 62 for supplying voltage to the electrodes of the sensor unit 60, measuring the current which flows and communicating the results to the surface via the wireline cable.

A wireline tool such as that diagrammatically illustrated by FIG. 12 could be configured and used to determine the producing zones of an oil production well. For vertical and near vertical wells, the tool is suspended from the wireline cable which is used to lower and raise the tool within the well. For highly deviated wells, the tool is pushed or pulled using coiled tubing from the surface, or a tractor powered and controlled by cable from the surface. In analogous manner a wireline tool could be configured and used to investigate an underground body of water contacted by a well drilled into an aquifer.

A sensor in accordance with this invention could also be incorporated into a wide variety of other tools and equipment. Possibilities include use in tools which are located permanently downhole, use in tools which are conveyed downhole at the head of coiled tubing, use in underground, undersea or surface pipeline equipment to monitor liquid flowing in the pipeline, and use in various kinds of process plant at the Earth's surface. A sensor in accordance with this invention may well be used outside the oil and gas industry. Use in water treatment can be envisaged, as can use in a wide variety of other areas of science and industry.

Figure 13:
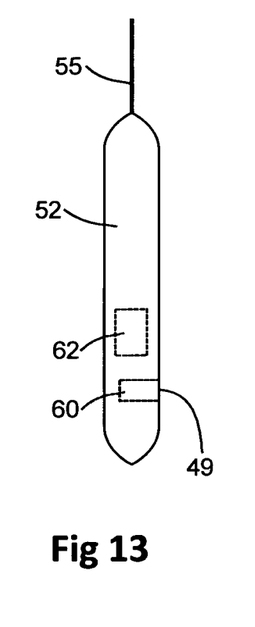
FIG. 13 is a diagrammatic illustration of a cable-suspended tool for testing water.

FIG. 13 illustrates a tool for investigating subterranean water. This tool also has a cylindrical body 52 which is suspended from a cable 55. A sensor unit 60 is accommodated within the body so that its end 49 is exposed to the subterranean water. The tool also encloses also encloses a unit 62 for supplying voltage to the electrodes of the sensor unit 60, measuring the current which flows and transmitting the results to the surface.

The invention claimed is:

1. An electrochemical sensor for pH of aqueous liquid comprising a solid, electrically conductive substrate, and two redox systems both located on a surface of the substrate wherein a first redox system is selected from the group consisting of aromatic quinones, aromatic diamines, catechols, phenothiazinium dyes and hydroxylamino-substituted aromatic groups and displays a reversible reduction or oxidation at a voltage which is sensitive to the concentration of hydrogen ions, and a second redox system is a metallocene which displays a reversible reduction or oxidation at a voltage which is essentially insensitive to the concentration of hydrogen ions wherein the first and second redox systems are directly connected together by a bond which consists of only one uninterrupted covalent bond extending from an aromatic ring of the first redox system to a ring of the metallocene which is the second redox system so that both redox systems are contained in the same chemical compound which is a compound of determinate structure with a molecular weight of less than 1000 and which contains no more than three instances of each redox system, wherein the first and second redox system each has a peak potential on its voltammetric redox wave at a respective pH, and wherein the peak potentials of the first and second redox systems do not overlap over pH range 1.0-9.9.

2. A sensor according to claim 1 wherein the chemical compound of determinate structure is monomeric with a molecular weight of less than 500.

3. A sensor according to claim 2 wherein the chemical compound contains only a single instance of each redox system.

4. A sensor according to claim 1 wherein the substrate is carbon based and the compound of determinate structure is bound to the substrate through covalent chemical bonds.

5. A sensor according to claim 1 wherein the first redox system is an aromatic quinone.

6. A sensor according to claim wherein the first redox system is a hydroxylamino-substituted aromatic moiety.

7. A sensor according to claim 6 wherein the first redox system is provided as a nitro-substituted aromatic moiety.

8. A sensor according to claim 1 wherein at least one of the redox systems is effective to catalyze an oxidation or reduction of a second species to be detected.

9. A sensor according to claim 8 wherein the second species is sulfide or oxygen.

10. A sensor according to claim 1 together with means to apply variable voltage to the sensor and measure current while the voltage is systematically varied.

11. A sensor according to claim 1 wherein the first redox system is selected from the group consisting of anthraquinone and its derivatives, phenanthrenequinone and its derivatives, phenothiazinium dyes and their derivatives, hydroxylaminobenzene and its derivatives, and nitrophenyl and its derivatives.

12. A sensor according to claim 8 wherein the sensor is for pH and oxygen, or for pH and sulfide, or for pH, oxygen and sulfide.

13. An electrochemical sensor for pH of aqueous liquid in contact with the sensor comprising a solid, electrically conductive substrate, and two redox systems both located on a surface of the substrate wherein a first redox system comprises at least one aromatic ring and displays a reversible reduction or oxidation at a voltage which is sensitive to the concentration of hydrogen ions, and a second redox system is a metallocene which displays a reversible reduction or oxidation at a voltage which is essentially insensitive to the concentration of hydrogen ions
wherein the first and second redox systems are directly connected together by a bond which consists of only one uninterrupted covalent bond extending from an aromatic ring of the first redox system to a ring of the metallocene which is the second redox system so that both redox systems are contained in the same chemical compound which is a compound of determinate structure with a molecular weight of less than 1000 and which contains no more than three instances of each redox system, and
wherein the substrate comprises conductive carbon and the compound of determinate structure is immobilized on the conductive carbon substrate.

14. A sensor according to claim 13 wherein the first redox system is an aromatic quinone or a hydroxylamino-substituted aromatic moiety.

15. A sensor according to claim 13 wherein the first redox system is selected from the group consisting of anthraquinone and its derivatives, phenanthrenequinone and its derivatives, phenothiazinium dyes and their derivatives, hydroxylaminobenzene and its derivatives, and nitrophenyl and its derivatives.

16. An electrochemical sensor for pH of aqueous liquid comprising a solid, electrically conductive substrate and a chemical compound with a molecular weight of less than one thousand located on a surface of the substrate wherein the chemical compound consists of
a first redox system which is selected from the group consisting of aromatic quinones, aromatic diamines, catechols, phenothiazinium dyes and hydroxylamino-substituted aromatic groups and displays a reversible reduction or oxidation at a voltage which is sensitive to the concentration of hydrogen ions, and
a second redox system which is a metallocene and which displays a reversible reduction or oxidation at a voltage which is essentially insensitive to the concentration of hydrogen ions
wherein the first and second redox systems are directly connected together and the connection between them consists of only one covalent bond which extends without interruption from an aromatic ring of the first redox system to a ring of the metallocene which is the second redox system, and
wherein the first and second redox system each has a peak potential on its voltammetric redox wave at a respective pH, and wherein the peak potentials of the first and second redox systems do not overlap over pH range 1.0-9.9.

17. An electrochemical sensor according to claim 16, wherein the first redox system is hydroxylamino substituted phenyl.

18. An electrochemical sensor according to claim 16, wherein the chemical compound is selected from hydroxylaminophenyl ferrocene, hydroxylaminophenyl diethyl ferrocene and hydroxylaminophenyl t-butyl ferrocene.

* * * * *